United States Patent [19]

Humphreys

[11] Patent Number: 5,559,028
[45] Date of Patent: Sep. 24, 1996

[54] METHODS OF ENHANCING OR ANTIGEN PRESENTATION TO T CELLS INHIBITING

[75] Inventor: Robert E. Humphreys, Acton, Mass.

[73] Assignee: Antigen Express, Inc., Wilmington, Del.

[21] Appl. No.: 64,400

[22] Filed: May 19, 1993

[51] Int. Cl.$^6$ .............................. C12N 5/06; C07K 7/00; A61K 38/10

[52] U.S. Cl. .................. 435/240.2; 435/724; 424/185.1; 424/193.1; 530/300; 530/326; 530/868; 514/2; 514/13

[58] Field of Search ................................. 424/88, 184.1, 424/185.1, 193.1, 278.1; 514/2, 8; 530/300, 350, 395, 868; 435/69.3, 7.24, 240.2

[56] References Cited

PUBLICATIONS

Reyes, et al., "Cathepsin B Cleavage of $I_i$ From Class II MHC α– and β–Chains[1]," *Journal of Immunology* 146: 3877–3880, (1991).
Elliott et al., "An Hypothesis on the Binding of an Amphipathic, α Helical Sequence in $I^i$ to the Desetope of Class II Antigens," *Journal of Immunology* 138: 2949–2952, (1987).
Thomas et al., "Proteolytic Cleavage of $I_i$ to p25," *Journal of Immunology* 140: 2670–2674, (1988).
Stille et al., "Hydrophobic Strip–of–Helix Algorithm for Selection of T Cell–Presented Peptides," *Molecular Immunology* 24: 1021–1027, (1987).
Reyes et al., "Selection of Class I MHC–Restricted Peptides with the Strip–of–Helix Hydrophobicity Algorithm," *Molecular Immunology* 25: 867–871, (1988).
Nguyen et al., "Inhibition by Leupeptin and Antipain of the Intracellular Proteolysis of $I_i$," *Human Immunology* 24: 153–163, (1989).
Quoc V. Nguyen and Robert E. Humphreys, "Time Course of Intracellular Associations, Processing, and Cleavages of $I_i$ Forms and Class II Major Histocompatibility Complex Molecules," *Journal of Biological Chemistry* 264: 1631–1637, (1989).
Reyes et al., "Prediction of Protein Helices with a Derivative of the Strip–of–Helix Hydrophobicity Algorithm," *Journal of Biological Chemistry* 264: 12854–12858, (1989).
Thomas et al., "Time–Dependent Cleavage of a High–Mannose Form of $I^i$ to p25 in an Intracellular Compartment," *American Journal of Hematology* 32: 167–177, (1989).
Goldschmidt et al., "Toward Engineering of T–Cell–Presented Epitopes," *Vaccines* 91: 339–343, (1991).
Lu et al., "Common Principles in Protein Folding and Antigen Presentation," *Tibtech* 9: 238–241, (1991).
Torgerson et al., "Highly Restricted Distributions of Hydrophobic and Charged Amino Acids in Longitudinal Quadrants of α–Helices," *Journal of Biological Chemistry* 266: 5521–5524, (1991).
Lam et al., "Highly Conserved, Potential Cleavage Sites about the Desetopes of MHC Class I and Class II Molecules," *Tissue Antigens* 39: 26–31, (1992).
Lu et al., "Number and Placement of Hydrophobic Residues in a Longitudinal Strip Governs Helix Formation of Peptides in the Presence of Lipid Vesicles," *Journal of Biological Chemistry* 266: 10054–10057, (1991).
Vazques et al., "Residues in the Longitudinal, Hydrophobic Strip–of–Helix Relate to Terminations and Crossings of α–Helices," *Journal of Biological Chemistry* 267: 7406–7410, (1992).
Rennell et al., "Critical Functional Role of the COOH–Terminal Ends of Longitudinal Hydrophobic Strips in α–Helices of T4 Lysozyme," *Journal of Biological Chemistry* 267: 17748–17752, (1992).
Goldschmidt et al., "Adsorption and Helical Coiling of Amphipathic Peptides on Lipid Vesicles Leads to Negligible Protection from Cathepsin B or Cathepsin D," *Immunological Investigations* 22: 25–40, (1993).
Nguyen et al., "Effects of Brefeldin A on Cleavage of Invariant Chain to p21 and p10 and the Appearance of $I_i$–Freed Class II MHC Dimers," *Molecular Immunology* 30: 137–144, (1993).
Editorial, "Hypothesis for the Control of Clotting Factor VIII Inhibitory Antibodies by Decreasing Potency of Helper T–Cell–Recognized Epitopes in Factor VIII," *Scand. J. Immunology* 36: 653–660, (1992).
Reyes et al., "Binding of Radioiodinated Influenza Virus Peptides to Class I MHC Molecules and to Other Cellular Proteins as Analyzed by Gel Filtration and Photoaffinity Labeling," *Molecular Immunology* 28: 341–348, (1991).
Lu et al., "Role of Recurrent Hydrophobic Residues in Catalysis of Helix Formation by T Cell–Presented Peptides in the Presence of Lipid Vesicles," *Journal of Immunology* 145: 899–904, (1990).
Alitalo et al., editors, "Synthetic Peptides in Biology and Medicine," published 1985 by Elsevier Science Publishers B. V. (Biomedical Division) (The Netherlands), pp. 191–197.
Adams, S. et al., Eur. J. Immunology 25:1693–1702 (1995), "Invariant chain peptides enhancing or inhibiting the presentation of antigenic peptides by major histocompatibility complex class II molecules".

Primary Examiner—Thomas M. Cunningham
Attorney, Agent, or Firm—Kevin M. Farrell

[57] ABSTRACT

The subject disclosure relates to the identification of mutations in the $I_i$ protein which result in an alteration of the endoprotease cleavage pattern of the mutant $I_i$ as compared with the endoprotease cleavage pattern of the wild type product. Methods for the identification of such mutants, and the mutants themselves are useful for the identification of classes of compounds to be further tested for immunomodulatory activity. A specific example of such a use is the screening of small organic compounds for the ability to bind to an intermediate in the $I_i$ endoprotease processing pathway. An small organic molecule having the ability to bind to such an intermediate can be further screened for the ability to modulate antigen presentation. The present invention also relates to the identification of immunomodulatory peptides. Peptides which either enchance or inhibit MHC Class II–restricted presentation of antigenic peptides are identified.

3 Claims, No Drawings

5,559,028

METHODS OF ENHANCING OR ANTIGEN PRESENTATION TO T CELLS INHIBITING

BACKGROUND OF THE INVENTION

Within certain cells, peptides from foreign or self antigens are bound intracellularly to MHC molecules and are then brought to the cell surface where the peptide and the presenting MHC molecules are recognized together as a complex by receptors on T lymphocytes. Generally, MHC type I molecules present endogenously synthesized antigen and MHC type II molecules present exogenous antigen. Peptide fragments of intracellular infectious organisms are transferred into the endoplasmic reticulum to bind to MHC class I molecules shortly after synthesis. Peptide fragments of endocytosed, extracellular antigen are created by proteolysis in a post-Golgi processing compartment where the fragments then become associated with MHC class II molecules. Most cells are capable of processing and presenting peptide fragments by MHC class I molecules, and specialized classes of antigen presenting cells also present exogenous antigen by the MHC class II pathway. For example, macrophages take up and present antigen to T cells which mature into helper or killer cells, and virgin B cells bind antigens to their surface immunoglobulins and then endocytose, digest and present fragments of that antigen via their MHC class II molecules to helper T cells. Those helper T cells release lymphokines and give direct intercellular molecular signals which stimulate the B cells to proliferate and mature into immunoglobulin producing plasma cell "factories". Antigen presentation by MHC class II molecules is crucial to initiation of many protective immune responses and to the origin of autoimmune responses.

An important regulator of antigen charging of the MHC class II $\alpha,\beta$ chain complex is the $I_i$ protein. This protein joins the MHC class II $\alpha,\beta$ chains at synthesis and is lost in a post-Golgi compartment where it might be digested with the same proteases which generate peptide fragments from foreign antigens. Blocking of the peptide binding site on the MHC class II $\alpha,\beta$ chains until the digestion of $I_i$ in the antigen processing compartment, presumably limits autoantigen presentation. That is, since MHC class II molecules can present endogenously synthesized, viral determinants the circumstances of binding might reflect either (1) transport of such determinants into the post-Golgi antigen binding compartment from the cytoplasm across the membrane of that compartment, or (2) transport of such peptides into the endoplasmic reticulum and 'premature' binding to MHC class II molecules upon 'early' release of $I_i$ or flow of such peptides perhaps in protected complexes to the post-Golgi antigen binding compartment.

SUMMARY OF THE INVENTION

The subject invention relates to a method for identifying sites which are cleaved during the release of $I_i$ from MHC class II $\alpha$ and $\beta$ chains. This can be accomplished, for example, by providing a recombinant DNA construct comprising a DNA sequence encoding $I_i$. The gene is then modified by performing site specific mutagenesis to alter the identity of an amino acid residue which is at or near a putative cleavage recognition site for a predetermined endoprotease in $I_i$, in a manner predicted to alter local secondary structure in the mutant $I_i$. A trimer complex comprising the mutant $I_i$, MHC class II $\alpha$ chain, and MHC class II $\beta$ chain is then formed by the coexpression of corresponding DNA sequences in a cell.

The trimer complex is then digested with an endoprotease in vitro. The sizes of the peptide fragments generated by digestion with the endoprotease is determined by conventional techniques and compared with the fragment sizes determined in e), with fragment sizes generated by digestion of wild type $I_i$ with the endoprotease to determine whether cleavage at a pre-existing cleavage site has been altered. A cleavage site determined in this manner represents a site which is cleaved during the release of wild type $I_i$ from MHC class II $\alpha$ and $\beta$ chains.

Such methods and mutants identified by such methods are useful for identifying classes of compounds, such as small organic compounds to be further tested for immunomodulatory activity. An initial step in such a method is to identify small organic compounds which bind selectively to an intermediate in the $I_i$ cleavage pathway. A compound identified in this manner is then contacted with an antigen presenting cell and determining the alteration of antigen presentation.

DETAILED DESCRIPTION OF THE INVENTION

It has been demonstrated that the immunoregulatory protein $I_i$, which joins the MHC class II $\alpha$ and $\beta$ chains at synthesis, is cleaved and released from the $\alpha,\beta$ chains by proteases (Thomas, L. J. et al., 1988, *J. Immunol.*, 140:2670–2674) including intracellular proteases cathepsins B and D (Reyes, V. E. et al., 1991, *J. Immunol.*, 146:3877–3880), presumably in the same intracellular compartments where protein antigens are digested into peptides which bind to the MHC class II molecules. Foreign peptides are found to bind to MHC class II molecules more efficiently when they are present during the cleavage and release of $I_i$ by cathepsin B. Binding of such peptides is not enhanced when present during digestion with cathepsin D alone but trace levels of cathepsin D further increases the level of binding of peptide catalyzed by cathepsin B. These observations led to the hypothesis of a staged cleavage and release of $I_i$ with concurrent insertion of foreign peptide into the MHC class II $\alpha,\beta$-$I_i$ fragment intermediate. The validity of this hypothesis is demonstrated herein by the design, creation and testing of mutants at the putative cleavage sites. The invention relies upon the identification of cleavage sites in $I_i$ on the basis of two-residue motifs (hydrophobic-cationic) for cathepsin B cleavage and two-residues motifs (hydrophobic-hydrophobic) for cathepsin D cleavage. Subsets of those cleavage sites are clustered in regions of the primary amino acid sequence of $I_i$ appearing to have local secondary structure and therefore to govern structure and function of the complex. The general structure of MHC class II $\alpha$ and $\beta$ chains consists of two proteins which insert at their C-termini through the cell membrane. Each of the two external, N-terminal portions of the $\alpha,\beta$ chains coil near the cell surface in a globular domain which supports a $\beta$-pleated sheet on which sits an $\alpha$-helix. The two chains are approximate mirror images and come together at one edge of the $\beta$-pleated sheet in such a fashion that the sheet supports the two $\alpha$-helices in an anti-parallel fashion (Brown, J. H. et al., 1988, *Nature* 332:845–850). An antigenic peptide binds between the anti-parallel helices (in the antigen binding site) and the entire complex (specifically certain residues on the foreign peptide and on the adjacent $\alpha$-helices) is recognized by a receptor on T lymphocytes. $I_i$ might block peptide charging to the MHC class II $\alpha,\beta$ chains by binding between the anti-parallel $\alpha$-helices until cleavage and release. Alternately, $I_i$ might interact with the MHC class II $\alpha,\beta$ chains in another fashion which indirectly (allosterically) regulates the capacity of the antigen binding site to receive peptides.

The invariant chain $I_i$ which is bound at synthesis to MHC class II $\alpha,\beta$ chains might direct the intracellular transport of MHC class II $\alpha,\beta$ chain complexes from their site of synthesis in the endoplasmic reticulum to a post-Golgi compartment where the complexes meet endocytosed and digested foreign antigen (Guagliardi, L. E. et al., 1990, *Nature,* 343:133–139). The presence of the $I_i$ chain on the MHC class II $\alpha,\beta$ complexes might prevent the binding of antigenic peptides in the antigen binding site of the MHC class II $\alpha,\beta$ chains (Teyton, L. et al., 1990, *Nature,* 348:39–44; Roche, P. et al., 1990, *Nature,* 345:615–619). In those reports complete removal of $I_i$ from class II $\alpha,\beta$ chains is proposed to occur before the binding of the foreign peptide. Demonstrating that foreign peptide binding occurs as a concerted event with, and is even catalyzed by, the removal of a fragment of proteolyzed $I_i$ is unique to this invention disclosure.

Cathepsins B and D can both digest antigenic proteins into immunogenic fragments and release $I_i$ from MHC class II $\alpha,\beta$ chains. Cathepsin B and cathepsin D generate antigenic peptide fragments (Takahashi, H. et al., 1989, *J. Immunol.,* 142:2221–2226; Roche, P. et al., 1990, *Nature* 345:615–619; Rodriguez, G. M. et al., 1992, *J. Immunol.,* 149:2894–2898). Cathepsins are found in the intracellular compartments where peptide charging to MHC class II molecules is thought to occur (Guagliardi, L. E. et al., 1990, *Nature,* 343:133–139). The thiol protease cathepsin B and the aspartyl protease cathepsin D generate p21 and other smaller fragments of $I_i$ (Roche, P. A. et al., 1991, *Proc. Natl. Acad. Sci.* USA, 88:3150–3154; Reyes, V. E. et al., 1991, *J. Immunol.,* 146:3877–3880). The cathepsin B inhibitor leupeptin limits the final proteolysis of $I_i$ to p21 and p14 fragments (Blum, J. S. et al., 1988, *Proc. Natl. Acad. Sci.* USA, 85:3975–3979; Nguyen, Q. V. et al., 1989, *Human Immunol.,* 24:153–163) and blocks antigen charging in vitro (Puri, J. et al., 1988, *J. Immunol.,* 141:3313–3319). Since cathepsin B but not cathepsin D was inhibited by leupeptin (Bond, J. S., 1989, Commercially available proteases. In: *Proteolytic Enzymes: A Practical Approach,* edited by R. J. Beynon, et al, pp. 232, IRL Press, New York), the intracellular cleavage of $I_i$ might involve the sequential action of cathepsin D and then cathepsin B. Cathepsin B digestion of purified $\alpha,\beta,I_i$ trimers generated a peptide binding site (Roche, P. A. et al., 1991, *Proc. Natl. Acad. Sci.* USA, 88:3150–3154).

Unique patterns of $I_i$ fragments, still associated with MHC class II $\alpha,\beta$ chains, or released from them, were seen after proteolytic release with cathepsins B or D (Reyes, V. R. et al., 1991, *J. Immunol.,* 146:3877–3880). Cathepsin B generated p21 and p6 fragments of $I_i$. Since both contained [$^{35}$S] cysteine and the only cysteine in $I_i$ is at C28, they were N-terminal and the p21 was most likely to be $M^1$-$K^{138}$. The p6 fragment could be $M^1$-R61. The transient p24 fragment could be $M^1$-$K^{154}$. The p21 and p10 $I_i$ fragments, which were increased greatly in leupeptin-treated cells after metabolic radiolabeling, might be accentuated due to partial inhibition by leupeptin of the endogenous cathepsin B which further degrades those fragments (Rudensky, A. Y. et al., 1991, *Nature,* 353:622–627; Chicz, R. M. et al., 1992, *Nature,* 358:764–768). Cathepsin D cleaved $I_i$ in two discrete patterns without an apparent mixture of cleavage sites within individual molecules. In addition, the N-terminal nature of a relatively basic, variably sialic acid-derivatized, N-terminal p25 was identified because it contained $C^{28}$, the only cysteine in $I_i$. This p25b form, containing [$^{35}$S] cysteine, could be derived from $M^1$-$W^{168}$ and $M^1$-$L^{173}$.

The present invention is based on the discovery that the process of antigen charging during $I_i$ release in the post-Golgi, MHC class II antigen-$I_i$ exchange compartment involves the sequential, or staged cleavage of $I_i$ from a trimer complex comprising $I_i$ and the MHC class II $\alpha,\beta$ chain. These results demonstrate that peptide binding to MHC class II $\alpha,\beta$ chains is a concerted process with the cleavage and release of $I_i$ by endoproteases present in antigen processing cells. Peptides are inserted into the antigen binding site at some stage in the release of $I_i$ fragments. The invention constitutes the method to determine stages in the cleavage and release of $I_i$ by the use of $I_i$ mutants at putative cleavage sites. Selected $I_i$ mutants after proteolytic treatment, thus resembling an intermediate in the $I_i$ cleavage/release-peptide charging mechanism, can be used for screening for small organic molecules which affect charging and presentation of antigen by the MHC class II $\alpha,\beta$ chains. Furthermore, homologs of fragments of $I_i$ can regulate the peptide charging process, or possibly other steps in the immune response.

Therefore, in one aspect, the present invention relates to a method for identifying sites which are cleaved during the release of $I_i$ from MHC class II $\alpha$ and $\beta$ chains. This method includes the use of a recombinant DNA construct which includes a DNA sequence encoding $I_i$ (see, e.g., Strubin et al., *EMBO J.* 3:869–872 (1984)). Site specific mutagenesis is carried out on the recombinant DNA construct, using conventional techniques, to alter the identity of an amino acid residue which is at or near a putative cleavage recognition site for a predetermined endoprotease in a manner predicted to alter cleavage site specificity in the mutant $I_i$. The highly repeated patterns of hydrophobic and positively charged adjacent amino acid residues, clustered around two local segments which resemble a tetraprolyl, cationic pseudohelix or kink and an amphipathic amphiphilic $\alpha$ helix, respectively, suggested that those sites are cleaved by cathepsin B. The runs of 3 adjacent hydrophobic residues at $Leu^{97}$ Leu Met and $Leu^{173}$ Leu Phe are consistent with the known cleavage site specificity of cathepsin D. Amino acid substitutions predicted to alter cleavage site specificity are generally selected on the basis of an R-group functionality which differs from that of the residue present in the wild type molecule. The most frequently selected amino acid substitution predicted to alter such specified cleavage sites is to replace an amino acid present in the wild type molecule with alanine.

The next step in the method for identifying sites which are cleaved during the release of $I_i$ from MHC class II $\alpha$ and $\beta$ chains is to form a trimer complex complex comprising mutant $I_i$ and MHC class II $\alpha$ and $\beta$ chain. This is most conveniently accomplished by the coexpression of the mutant $I_i$ gene described above, and MHC class II $\alpha$ and $\beta$ chains. This coexpression is accomplished using conventional methods, preferably in cultured mammalian cells such as COS cells. DNA encoding MHC class II $\alpha$ and $\beta$ chains can be obtained from the American Type Culture Collection (ATCC) in Rockville, Md. The three genes which encode the components of the trimer complex are arranged within DNA expression constructs which contain the regulatory sequences which are known to be required for expression (preferably both in vivo or in vitro), as well as a selectable marker. The use of cultured cells is considered to be in vitro use in the context of this disclosure. The constructs are then used to transfect mammalian cells in culture. The cells are grown for an appropriate period following transfection and metabolically radiolabeled (for example using [$^{35}$S]methionine). Microsomal membranes are then prepared from the radiolabeled cells by conventional methods, and then solubilized in a nonionic detergent. At this stage, the presence of assembled trimer complex can be confirmed by immunobiochemical methods (e.g., by immunoprecipitation). Antibodies reactive with components of the trimer complex which are useful for this confirmation are available from the ATCC and from commercial sources.

Assembled trimer complex present as a component of the detergent solubilized microsomal membrane preparation is then digested with an endoprotease which is thought to be an intracellular protease present in antigen processing cells. Preferred endoproteases include cathepsins B and D. Such enzymes are available commercially and are provided with protocols describing appropriate incubation conditions. Digestion periods and enzyme concentrations can be varied to reveal the spectrum of endoproteolytic digestion products ranging from intermediate fragments to the smallest peptide detected. The size of the digestion products is determined, for example by SDS-gel electrophoresis (e.g., in a polyacrylamide electrophoretic medium). By correlating banding patterns with digestion time it is possible to deduce the sequential patterns of cleavage of the $I_i$ molecule by the respective proteases.

The sizes of the peptide fragments determined in this manner are then compared with fragment sizes generated by digestion of wild type $I_i$ with the endoprotease to determine whether cleavage at a pre-existing cleavage site has been altered. A cleavage site which is determined by this comparison represents a site which is cleaved during the release of wild type $I_i$ from MHC class II α and β chains.

As described in the Examples which follow, several mutant $I_i$ molecules have been identified in the manner described above. The nomenclature employed herein employs the single letter amino acid code. Each mutant identified in this manner is designated by the letter "M" (for mutant) followed by bracketed information specifying the particular mutations present in the mutant. For example, $M[R^{19}\rightarrow A;R^{20}\rightarrow A]$ denotes a mutant $I_i$ in which arginine at position 19 is replaced by alanine and arginine at position 20 is replaced by alainine. Other mutants specifically identified which exhibit an endoprotease digestion pattern which differs from that of the wild type are: $M[R^{78}\rightarrow A;K^{80}\rightarrow A;K^{83}\rightarrow A;K^{86}\rightarrow T]$; $M[K^{137}\rightarrow A;K^{143}\rightarrow A]$; $M[R^{151}\rightarrow A;K^{154}\rightarrow A]$; and $M[L^{174}\rightarrow V;F^{175}\rightarrow A]$.

Another aspect of the present invention relates to methods for identifying small organic compounds which bind selectively to an intermediate in the $I_i$ cleavage pathway. Such intermediates may, for example, mimic a rate-limiting step in the cleavage/release - peptide charging process. Small organic compounds as used herein are organic compounds, preferably less than 3,000 molecular weight and most preferably less than 1,000 molecular weight which are derived by chemical synthesis or obtained as extracts from biological sources. Libraries of such small organic compounds, organized on structural features, are maintained and routinely used for such screening purposes.

A preferred method for identifying such small organic compounds is to develop an inhibition binding assay using, for example, a T-cell presented peptide or homolog thereof. A T cell presented peptide is a peptide which has been demonstrated to contain a unique epitope recognized by a T-cell hybridoma in the context of a MHC class II molecule. These can be generated for example by protease digestion and isolation, or by chemical synthesis. As used herein, a homolog of a T cell-presented peptide is defined as a peptide having amino acid substitutions, fragments of such peptides or a small organic compound which is thought to bear structural homology to a segment of the T cell-presented peptide. Such an inhibition assay is carried out by combining the following components in vitro 1) an endoprotease digested first trimer complex comprising a mutant $I_i$ having an endoprotease digestion pattern which differs from that of wild type, and MHC class II α and β chains, 2) a small organic molecule to be tested for inhibition of T cell-presented peptide binding and 3) a T cell-presented peptide. In such an assay, if the binding of the T cell-presented peptide to the endoprotease digested trimer complex is blocked in the presence of the small organic compound, it can be concluded that the small organic compound is binding to an intermediate in the staged cleavage process. Indicator assays such as an ELISA assay can be used to identify compounds which block the binding of the indicator compound. Such an assay is carried out by linking to a solid support a purified molecule to be tested for binding affinity to the T-cell presented peptide (or homolog thereof). The T-cell presented peptide (or homolog thereof) present in a solution is then incubated with the molecule linked to the solid support under conditions appropriate for binding. Such binding is determined through the recognition of an indicator attached to the T cell-presented peptide or homolog thereof.

The selectivity of binding referred to above is defined relative to the binding of the small organic compound to a second trimer complex comprising wild type $I_i$, MHC class II α and β chains; and a dimer comprising MHC class II α and β chains. Compounds which exhibit a binding affinity for endoprotease digested first trimer complex which is at least about 3-fold higher than the binding affinity for a second trimer complex comprising wild type $I_i$, MHC class II α and β chains; and a dimer comprising MHC class II α and β chains meet the selectivity requirement of the present method. Binding affinity determinations can be made using a variety of well known techniques (e.g., ELISA).

The binding affinity determination is carried out separately for each of the following complexes: 1) protease digested first trimer complex, second trimer complex (containing wild type $I_i$), and MHC class II α and β chains. Mutant $I_i$-containing complexes which demonstrate the required selectivity are identified. Such mutants are then used in a similar inhibition binding assay. More specifically, in the case of an ELISA inhibition binding assay, the mutant complex is fixed to a solid support, followed by incubation with a selected small organic molecule. The concentrations of the small organic molecule would be determined empirically. The goal of this screening step is to identify a small organic molecule which binds to the mutant $I_i$-containing complex thereby inhibiting the binding of the T cell-presented peptide (or homolog thereof) to the mutant $I_i$-containing complex.

Small organic compounds identified in the binding inhibition assay described above can be tested for immunomodulatory activity. A variety of assays (both in vivo and in vitro) which can be used for this purpose are known in the art. One example of such an assay involves the analysis of the modulation of presentation of an immunogenic peptide by an antigen presenting cell to a responder T lymphocyte. More specifically, a small organic compound to be tested for immunomodulatory activity is contacted with a cell culture comprising a known T-cell immunogenic peptide, its restricting antigen presenting cell, and T cells responding specifically to the immunogenic peptide in the context of the antigen presenting cell. In the absence of an inhibitory compound, the combination of components referred to will result in T-cell stimulation. T-cell stimulation can be detected, for example, by measurement of interleukin release from a T-cell. If, however, the small organic compound has an immunomodulatory effect, the basal level of T cell stimulation without the inhibitor is detectably altered. Detectably altered, as used herein, means a change of more than one standard deviation in the measured level of T cell activation in the mixture containing the small organic compound relative to the level of T cell activation in the control sample which does not contain the small organic molecule.

In another aspect, the present invention relates to the identification of immunomodulatory peptides. Given the hypothesis that $I_i$ release from MHC class II molecules occurs as a staged process with the insertion of an immunogenic peptide into the antigen binding site of an MHC class II complex, it is reasonable to propose that peptides of $I_i$ bind at selected locations in intermediate complexes and thereby modulate the process of antigen presentation. To test this hypothesis $I_i$ peptides and homologs thereof are contacted with an antigen presenting assay of the type described above to determine immunomodulatory activity.

Using an assay of this type, peptides of $I_i$ having immunomodulatory activity have been identified. Both enhancers and inhibitors of antigen presentation have been identified. For example, peptides which enhance antigen presentation include [Tyr-$I_i$(78–92), (YRMKLPKPPKPVSKMR)(SEQ. ID. NO:1)]; and peptides which inhibit antigen presentation are [$I_i$(148–164), (ENLRHLKNTMETLDWKV) (SEQ. ID. NO:2)] and [LYELQTKLQTLK (SEQ. ID. NO:3)]. It is noted that Sette et al. ((1992) Science 258:1801–1804) have reported a peptide of $I_i$ having an inhibitory effect on the binding of a T-cell presented peptide. However, the disclosure of an $I_i$ peptide which enhances antigen presentation has heretofore not been reported in the literature. It is likely that one skilled in the art could obtain a homolog of [Tyr-$I_i$(78–92), (YRMKLPKPPKPVSKMR) SEQ. ID. NO:1)] which inhibits antigen presentation by systematic replacement of amino acid residues which retain binding of the MHC class II α and β chains but do not permit the function associated with enhancement of antigen presentation.

The disclosure of the present invention has implications relating to the treatment of autoimmune disease. The development of therapeutic drugs to block MHC class II α,β-mediated antigen presentation to T cells will be greatly enhanced by the use of such transition complex homologs offered by these mutant $I_i$ molecules in which progression is blocked to a subsequent step, for example, where a structural change in the class II α,β chains locks the antigenic peptides into the antigen binding site.

The MHC class II-mediated presentation of endogenous autoantigenic determinants by certain cells in which MHC class II α and β chains are induced with a relative or absolute lack of $I_i$. While most models for the MHC class II-mediated presentation of antigen involve internalizing and digesting exogenous antigen which becomes bound to class II α,β chains in a post-Golgi/endosomal compartment, antigens endogenously synthesized by the antigen-presenting cell are also presented. Fragments of those antigens which are transported into the endoplasmic reticulum for binding to MHC class I molecules are normally not bound to MHC class II α,β chains because the $I_i$ molecule prevents insertion into the antigen binding site during transport and processing of the class II molecules. In certain cells, for example, pancreatic β cells, under certain pathological conditions MHC class II α,β chain may be induced with an absolute or relative lack of $I_i$. The endogenous peptides, otherwise destined for binding to class I MHC molecules, could then become bound also to the MHC class II α,β chains and subsequently presented to T cells thereby inducing an autoimmune response.

This presentation of endogenous antigen under such abnormal pathological conditions can be inhibited by replacing the function of $I_i$ with proteins generated from mutant $I_i$ genes, or with peptide fragments or compounds identified with screens using such structures or designed from such structures. For example, this condition can be corrected in such cells by the expression of $I_i$ mutants which are not completely cleaved but remain bound to class II MHC α,β chains, e.g., M[$R^{78} \rightarrow A; K^{80} \rightarrow A; K^{83} \rightarrow A; K^{86} \rightarrow T$], and which do not permit (or inhibit) charging of peptide or presentation of charged peptide at the cell surface to T cells. Not being bound by theory, wild type $I_i$ or $I_i$ mutants which are selected for the characteristic of retention to MHC α,β chains are expressed in a cell proposed to present autoantigens in order to block the binding of peptides to the MHC class II α,β chains during their transport and processing other than in the post Golgi/endosomal compartment in which the binding of antigen is thought to occur under normal physiological conditions. In the case of pancreatic β cells, the gene for wild type $I_i$ or a selected $I_i$ mutant is expressed under the control of the promoter for insulin using established molecular biological techniques to create that construct. The insulin promoter-$I_i$ gene construct is inserted by transgenic or equivalent methods. Optimal conditions for the refinement of this method to block MHC class II presentation of autoantigens are established in the nonobese diabetic mouse model and are then applied to human subjects for the treatment of diabetes mellitus and other autoimmune disorders.

EXAMPLES

Example 1

Peptide Binding During $I_i$ Release By Cathepsin B

The efficiency of peptide binding was tested during cathepsin B-mediated release of $I_i$ from solubilized MHC class II α,β,$I_i$ complexes. Digestions with varying concentrations of cathepsin B at pH 5.0 [A: no enzyme (peptide only); B: cathepsin B (0.1 U/ml); C: cathepsin B (0.5 U/ml); D: cathepsin B (2.5 U/ml)] for 5, 15, 30, or 60 min at room temperature or 37° C. were carried out in the presence of the N-hydroxysuccinimido azidobenzoyl (HSAB)-labeled, $^{125}$I-radiolabeled, influenza virus MA(18–29) peptide which was subsequently crosslinked where it became bound. This HLA-DR1-restricted, T cell-presented peptide was tested with the DR-1-positive Jesthom cell line. The radioiodinated peptide (100 nM) was added to the solubilized microsomal membrane proteins from Jesthom cells with cathepsin B which cleaved $I_i$ for varying periods of time. After each incubation, the enzyme was inactivated by 1:1 dilution with 10 mM Tris, pH 9.0, containing 2 mM PMSF, 10 mM N-ethylmaleimide acid and 1 mM iodoacetamide. The peptides were then crosslinked to the α,β chains after ultraviolet light activation of the azido group. Crosslinked peptide was detected at 5 min of digestion with progressive increases in levels of peptide crosslinked to the MHC class II α and β chains. At comparable time points and temperatures about 10 times as much peptide bound with 0.05 U/ml cathepsin B than with peptide alone, without the enzyme. Peptide binding increased proportionately with the amount of enzyme, the duration of the incubation, and the temperature of incubation.

Example 2

Addition of Peptide After Inactivation of Cathepsin B

Peptide binding was not detected without cathepsin B treatment and much greater amounts of peptide was bound when the peptide was present during $I_i$ proteolysis. The binding of peptide to MHC class II $\alpha,\beta$, $I_i$ trimers was compared to binding to MHC class II $\alpha,\beta$ dimers from which $I_i$ had been released with cathepsin B. Detergent-solubilized microsomal membranes containing MHC class II $\alpha,\beta,I_i$ trimer were incubated with cathepsin B (0, 0.1, 0.5, 2.5 U/ml) for 30 min, pH 5.0, room temperature, in the presence of $^{125}$I-labeled HSAB-MA(18–29) peptide (100 nM). After that incubation, the peptide was crosslinked by photoactivation where it was bound, and samples were immunoprecipitated with anti-class II mAb, subjected to SDS-PAGE, and the dried gels were autoradiographed. Alternately, after 30 min incubation with solubilized microsomal membranes, the enzyme was inactivated by 1:1 dilution with 10 mM Tris, pH 9.5, containing 2 mM phenylmethylsulfone, 10 mMN-ethylmaleimide and 1 mM iodoacetamide. $^{125}$I-labeled HSAB-MA(18–29) was added for 30 min more and photoactivated for peptide crosslinkage. Immunoprecipitates of these samples with anti-MHC class II antibody were processed as above. The peptide was bound about 3 times more efficiently to MHC class II $\alpha,\beta$ chains when present during the cathepsin B digestion than when added afterwards, as judged by densitometry of the autoradiographs from the digestions with 0.5 U/ml or 2.5 U/ml of cathepsin B. The peptide did not bind to MHC class II $\alpha,\beta,I_i$ complexes which were not treated with cathepsin B.

Example 3

Peptide Binding During $I_i$ Release by Cathepsin D

Peptide binding was not enhanced during $I_i$ cleavage by cathepsin D. Detergent-solubilized microsomal membranes containing MHC class II $\alpha,\beta,I_i$ trimer were incubated with varying amounts of cathepsin D for 30 min in the presence of $^{125}$I-labeled HSAB-MA(18–29) peptide (100 nM), crosslinked and processed as above. Under a wide range of concentrations of cathepsin D which cleaved $I_i$ but did promptly not lead to complete dissociation of its fragments from MHC class II $\alpha,\beta$ chains (Reyes, V. E. et al., 1991, *J. Immunol.*, 146:3877–3880), no enhanced binding of the radioiodinated MA(18–29) peptide was seen.

The finding that peptide binding to MHC class II $\alpha,\beta$ chains was enhanced by the presence of the peptide during cathepsin B (but not cathepsin D) treatment lead to the conclusion that cleavage and release of these fragments constitutes a concerted process with charging of the MHC class II molecules with antigenic peptides.

Example 4

Competition for Peptide Binding

The specificity of [$^{125}$I]MA(18–29) binding to MHC class II molecules of HLA-DR1$^+$ Jesthom, human B lymphoblastoid cells was tested by competition with: MA(18–29) peptide, HLA-DR1-restricted influenza HA(306–318), HLA-DP-restricted dengue virus NS3(251–265), and HLA-B37-restricted influenza virus NP(336–356). These peptides and $^{125}$I-labeled HSAB-MA(18–29) peptide (100 nM) were incubated for 30 min with detergent-solubilized microsomal membranes containing MHC class II $\alpha,\beta,I_i$ trimer in the presence of 0.5 U/ml cathepsin B, photoactivated for crosslinkage and immunoprecipitates with anti-MHC class II antibody were processed as above. Competition for binding was only seen with the HLA-DR1-restricted peptides, i.e., peptides which were shown by others to be recognized by T lymphocytes after binding human MHC class II HLA-DR1 molecules. That is, the binding of [$^{125}$I]HSAB-MA(18–29) ($10^{-7}$ M) to MHC class II molecules was competed with cold HSAB-conjugated MA(18–29) and influenza virus HA(306–318) but not influenza virus NP(336–356) and dengue virus NS3(251–265).

Example 5

Further Enhancement of Cathepsin B-Mediated Peptide Binding Effect by Addition of Cathepsin D The lowest level of cathepsin D seen to cleave $I_i$ was 0.1 U/ml. Solubilized microsomal membrane proteins from [$^{35}$S]methionine-labeled Jesthom cells were treated with the cathepsin D (concentrations 0, 0.01, 0.05, 0.1, 0.5, 2.5, 10.0 U/ml) at pH 5.0 for 30 min at room temperature. At the end of the incubation, the enzyme was inactivated and immunoprecipitates with anti-class II mAb, IVA12 or with anti-$I_i$ mAb, VIC-Y1 were formed. The immunoprecipitated samples were analyzed by SDS-PAGE and autoradiography. In a second experiment, when the lowest level of cathepsin D (0.1 U/ml) seen to cleave $I_i$ was added to the assay for peptide binding in the presence of varying concentrations of cathepsin B (0.02–0.5 U/ml), the net level of peptide binding was enhanced about 3 times that seen without cathepsin D, as judged by densitometry of the autoradiographs. For this experiment iodinated HSAB-MA(18–29) peptide and unradiolabeled microsomal membranes were incubated with or without 0.1 U/ml cathepsin D for 10 min or 30 min in the presence of varying amounts of cathepsin B (0.02, 0.1, or 0.5 U/ml). After subsequent photoactivation and immunoprecipitation with anti-class II mAb, the samples were subjected to SDS-PAGE and autoradiography.

Example 6

Identification of $I_i$ Cleavage Sites by Analysis of the Primary Sequence of $I_i$ into Account Apparent Secondary Structural Elements and Cleavage Motifs for Cathepsins B and D Putative cleavage sites in the sequence of $I_i$ were proposed for the staged cleavage and release of $I_i$ by cathepsin D and cathepsin B in order to test the hypothesis that foreign peptide charging of the MHC class II $\alpha,\beta$ chain antigen binding site was a concurrent process with the cleavage and release of $I_i$. Since cathepsin B and cathepsin D cleaved $I_i$ from MHC class II $\alpha,\beta$ chains with a series of $I_i$ fragments unique to each enzyme (Reyes, V. E. et al., 1991, *J. Immunol.*, 146:3877–3880), $I_i$ has cleavage sites specific for each enzyme. Cathepsin B cleavage at hydrophobic-cationic sites and cathepsin D cleavage at hydrophobic-hydrophobic sites can be proposed (Table I).

TABLE I

Potential Cathepsin B and Cathepsin D Cleavage Sites in $I_i$

```
        10        20        30        40        50        60
                   \
MDDQRDLISNNEQLPMLGRRPGAPESKCSRGALYTGFSILVTLLLAGQATTAYFLYQQQG
        /                    // //              /

70        80        90       100       110       120
               \ \  \  \  \  \
 \
RLDKLTVTSQNLQLENLRMKLPKPPKPVSKMRMATPLLMQALPMGALPQGPMQNATKYGN
                                //

130       140       150       160       170       180
                   \     \   \ \        \         \
MTEDHVMHLLQNADPLKVYPPLKGSFPENLRHLKNTMETLDWKVFESWMHHWLLFEMSRH
        /                                            //

190       200       210
SLEQKPTDAPPKESLELEDPSSGLGVTKQDLGPVPM        (SEQ ID NO. 4)
```

In Table I, Cathepsin B sites are indicated by \ the sequence and cathepsin D sites are indicated by / below the sequence. In each case, cleavage is hypothesized to occur at the carboxyl side of the indicated residue. The transmembranal region $Gly^{31}$-$Gln^{57}$, the hexa-cationic, tetraprolyl kink $Leu^{77}$-$Met^{93}$, and the α-helix $Phe^{146}$-$Val^{164}$ are underlined.

Cleavage might also be restricted by local $I_i$ structures (Table I), including: the transmembranal helix $A^{32}$-$L^{55}$; a tetraprolyl palindrome ($L^{81}$-$M^{93}$) with potential cathepsin B cleavage sites $LR^{78}$, $MK^{80}$, $PK^{83}$, $PK^{86}$, $VSK^{90}$, $MR^{92}$; a second tetraprolyl region $P^{96}$-$P^{111}$; an amphipathic helix $F^{146}$-$V^{164}$ with potential cathepsin B cleavage sites $LK^{137}$, $LK^{143}$, $LR^{151}$, $LK^{154}$, $WK^{163}$, $VK^{165}$; and a C-terminal tail with potential cathepsin D cleavage site $LLF^{175}$. In order to address the functions of these putative cleavage sites, the following $I_i$ gene mutations were generated: [$R^{78}$→A;$K^{80}$→A;$K^{83}$→A;$K^{86}$→T], [$K^{137}$→A;$K^{143}$→A], [$R^{151}$→A;$K^{154}$→A], and [$L^{174}$→V;$F^{175}$→A]. The cathepsin B and cathepsin D cleavage patterns of the protein products in COS1 cells transfected with mutant $I_i$ and wild type HLA-DR α and β genes demonstrated staged cleavage of $I_i$ by cathepsin D and cathepsin B. One can hypothesize if cathepsin D cleaves first at $LLF^{175}$, then cathepsin B cleavage at $LK^{137}$ and $LK^{143}$ could release putative helix $Phe^{146}$-$Leu^{164}$ followed by peptide insertion into the antigen binding site. That helix would be rapidly destroyed by cathepsin B digestion at the six LR or LK positions in and around the helix. Final cleavages in the tight, tetraprolyl palindrome $L^{81}$-$M^{93}$ at one or more of six LK or LR sites could lead to generation of small $I_i$ fragments which remain associated with α,β chains. MA(18–29) might bind to MHC class II α,β chains at the stage of cathepsin B cleavage at $LK^{137}$ and $LK^{143}$ or cathepsin B cleavage at the tetraprolyl palindrome $LK^{137}$-$M^{93}$. Further functional studies with these and related $I_i$ mutants will resolve the mechanism for peptide insertion into the MHC class II antigen binding site and lead to assays for the selection of allele-non-specific immunosuppressive agents.

Mutations were constructed in the $I_i$ gene corresponding to one putative cathepsin D site and three clusters of putative cathepsin B sites were constructed. A mutation was also made at the cytoplasmic dibasic site $R^{19}R^{20}$. Four strategic principles were used in the design of the mutants. (1) Putative cleavage sites should lead to the fragments found experimentally after cathepsin B or cathepsin D digestion. For example, since cathepsin B produces a N-terminal 21 kDa fragment of $I_i$ (Reyes, V. E. et al., 1991, *J. Immunol.*, 146:3877–3880), cleavages at $K^{137}$ or $K^{143}$ could produce that fragment. (2) Protease-specific cleavage motifs were identified. Cathepsin B was suspected to attack the unusual frequency of clustered LK and LR residues and cathepsin D was reported to prefer paired hydrophobic residues except when the C-terminal one is Val, Gly or Ala (Bond, J. S., 1989, Commercially available proteases. In: *Proteolytic Enzymes: A Practical Approach*, edited by R. J. Beynon, et al., pp. 232, IRL Press, New York). (3) The facts that both p21 and naturally occurring $I_i$ digestion products, e.g., $L^{97}$-$G^{119}$, bound to MHC class II α,β chains (Chicz, R. M. et al., 1992, *Nature*, 358:764–768), led to the suggestion that cleavage sites producing p21 and p25 are C-terminal to that region. (4) Hypothesizing local $I_i$ structures with clusters of putative cathepsin B cleavage sites (Table I) led to a model for the staged cleavage and release of $I_i$ by cathepsin B and cathepsin D.

Example 7

Expression of Wild Type and Mutant $I_i$ Chains With or Without HLA-DR α,β Chains in COS1 Cells The mutant $I_i$ genes constructed with oligonucleotides of Table II were transfected with HLA-DR1 α and β genes into COS1 cells after incorporation into a RSV.5(neo) plasmid into which human HLA-DR1 α, β genes (RSV-5(neo)-DRα120 and RSV.5(gpt)-DRα008) had been cloned and driven by Rous sarcoma virus (RSV) long terminal repeat (LTR) sequences (Long et al., 1991). The $I_i$ gene (45 1-p33-143) (Sekaly et al., 1986) was used for making $I_i$ mutations. The mutant and WT $I_i$ genes were cloned into a RSV.5 (hygromycin) vector. All the genes and the cloning vector were the gift of Dr. Eric Long of NIH. The HLA-DR1 α and β genes were reconstructed into one plasmid by digestion of RSV.5 (neo) DR1α 120 with Nde 1 to linearize the plasmid and of RSV.5 (gpt) DR1β 008 with Nde 1 and Bgl II to release the DR1β gene. Linearized RSV.5 (neo) DR1α 120 plasmid was treated with calf intestinal phosphatase and ligated to the purified DR1β gene fragment. The product was treated with T4 DNA polymerase to fill the unmatched ends, and religated.

Site-directed mutagenesis was performed by the polymerase chain reaction (PCR) method of Ho et al. (1989) using the oligodeoxynucleotides of Table II. PCRs were carried out using Taq polymerase according to the manufacturer's instructions (Perkin Elmer Cetus, Norwalk Conn.). One oligodeoxynucleotide (oligo A) corresponding to the RSV.5 vector sequence at Sal 1 site was synthesized to polymerize in a 3' direction during the PCR and a second DNA oligodeoxynucleotide (oligo B) corresponding to the sequence of the 3' untranslated region of the $I_i$ gene from 26 nucleotide to 43 nucleotide 3' to the stop codon (Strubin et al., 1984) was synthesized to polymerize in a 5' direction during the PCR. Sal 1 and BamH 1 sites were created in these two oligodeoxynucleotides, respectively, for cloning purposes. Other oligodeoxynucleotides were synthesized according to the sequences where the mutations were to be made (Table 1). PCR reactions were performed in 50 µl volumes containing: 50 mM KCl, 10 mM Tris-NaCl, pH 8.3, 4 mM $MgCl_2$, 100 µM of each dNTP, 200 ng of each oligonucleotide, and 2.5 units of Taq polymerase. These samples were overlaid with 50 µl of mineral oil. PCR reactions were performed using a DNA Thermal Cycler (Perkin Elmer Cetus) programmed as follows: one cycle of denaturation (94° C., 2 min); annealing (temperature was calculated according to Ho et al., 2 min); extension (72° C., 2 min). Another 30 cycles of amplification were followed under conditions for the first cycle except 94° C. was set for 1 min. Mutagenesis was carried out in two steps: amplification of DNA fragments from the plasmid template and overlap extension joining DNA fragments purified in a low melting gel. Second round PCR products were digested with Sal 1 and BamH 1 and ligated to an RSV.5 vector, which contained a hygromycin resistance gene (Long et al., 1991) and was digested with Sal 1 and BamH 1. All molecular biological techniques were performed according to Sambrook et al. (1989) and mutations were confirmed by DNA sequencing.

Table II

OLIGONUCLEOTIDES USED IN THE GENERATION OF $I_i$ MUTANTS

Hybridizing in the flanking regions of the $I_i$ gene:

oligo A:

5'-CAGGTCGACTCTAGACGATCC-3' (Seq. ID NO. 5)

oligo B:

5'-GTAGGATCCTGTGTGGGGCTGGCAG-3' (Seq. ID NO. 6)

Pairs of oligonucleotides used for each mutation:

1) $M[R^{19} \rightarrow A; R^{20} \rightarrow A]$
   oligo 1: 5'-CTG GGC GCG GCC CCT GG-3'  (SEQ ID NO. 7)
   oligo 2: 3'-GAC CCG CGC CGG GGA CC-5'  (SEQ ID NO. 8)

2) $M[R^{78} \rightarrow A; K^{80} \rightarrow A; K^{83} \rightarrow A; K^{86} \rightarrow T]$
   oligo 3: 5'-C ATG GCG CTT CCC GCG CCT CCC ACG CC  (SEQ ID NO. 9)
   oligo 4: 3'-G GAC CGC TAC CGC GAA GGG CGC-5'  (SEQ ID NO. 10)

3) $M[K^{137} \rightarrow A; K^{143} \rightarrow A]$
   oligo 5: 5'-G GTG TAC CCG CCA CTG GCG GG-3'  (SEQ ID NO. 11)
   oligo 6: 3'-G GAC CGC CAC ATG GGC GGT G-5'  (SEQ ID NO. 12)

4) $M[R^{151} \rightarrow A; K^{154} \rightarrow A]$
   oligo 7: 5'-CTG GCA CAC CTT GCG AAC-3'  (SEQ ID NO. 13)
   oligo 8: 3'-GAC CGT GTG GAA CGC TTG-5'  (SEQ ID NO. 14)

5) $M[L^{174} \rightarrow V; F^{175} \rightarrow A]$
   oligo 11: 5'-GG CTC CTG GCT GAA ATG-3'  (SEQ ID NO. 15)
   oligo 12: 3'-CC GAG CAC CGA CTT TAC-5'  (SEQ ID NO. 16)

COS1 cells were obtained from Dr. P. Newberger of the University of Massachusetts Medical Center (Worcester, Mass.). The cells were maintained in RPMI-1640 medium supplemented with 2% fetal calf serum and 8% bovine calf serum (Hyclone Laboratories, Inc., Logan, Utah) in 10 cm tissue culture dishes (Falcon, Lincoln Parker) at 37° C. in a 5% $CO_2$ atmosphere. COS1 cells did not express $I_i$ as tested by immunoprecipitations with either VIC-Y1 or E1 antibodies. VIC-Y1 recognizes all $I_i$ molecules, while E1 recognizes only high mannose forms of $I_i$. VIC-Y1 mAb to an N-terminal $I_i$ determinant (Quaranta et al., 1984) was the gift of Dr. Walter Knapp in An Der Grub, G.m.b.H. (Kaumberg, Austria). E1 anti-human $I_i$(183–193) serum was prepared previously (Thomas et al., 1988). IVA12 mAb to human MHC class II molecules was produced as ascites from the hybridoma HB145 from the ATCC.

Gene transfection was carried out by electroporation according to Xu and Stavnezer (1992). COS1 cells were grown for 24 h, released with trypsin-EDTA (GIBCO, BRL), washed twice with warmed RPMI-1640 medium without serum, and resuspended in RPMI-1640 medium without serum at $6 \times 10^6$ cells/ml. Transfections were carried out at 250 V/1200 µF/ml volume with a PG200 Progenitor II electroporater (Hoefer Scientific Instruments, San Francisco, Calif.). Each plasmid was used at 24 µg per $6 \times 10^6$ cells. After transfection, cells were recultured in complete RPMI-1640 medium at $3 \times 10^6$ cells/8 ml/dish. Electroporation efficiently introduced DNA into the COS1 cells. 40–65% of COS1 cells expressed HLA-DR1 molecules at the cell surface 45 h after transfection as determined by immunofluorescent staining.

45 h after transfection, cells were labeled for 3 h with [$^{35}$S]methionine (Sambrook et al., 1989). After pouring off the medium, the dishes were washed twice with 10 ml of warmed, methionine-free, serum-free RPMI-1640 medium and 1.5 ml of warmed, methionine-free RPMI-1640 medium containing 2% FCS and 8% BCS (both dialyzed) was added. Dishes were incubated for 20 min at 37° C. in 5% $CO_2$. To each dish was added 0.15 mCi of [$^{35}$S]methionine (NEN, MA), followed by incubation for 3 h with the rocking of the dishes about every 20 min. After 3 h the dishes were washed twice with cool PBS and then 1 ml of lysis buffer (10 mM Tris-HCl, pH 7.4, and 0.5% Triton-X100) was added. The dishes were held on ice for 20 min and the cells were scraped from the dish and transferred to a tube. After vortexing for 1 min, lysates were centrifuged in a microcentrifuge at 4° C. for 10 min. The supernatants were collected in a second tube and cleared with formalinized *Staphylococcus aureus* Cowen Strain A (Chemicon, El Segundo, Calif.) and used immunoprecipitations. Immunoadsorbants were prepared by incubating 100 µl of protein A-sepharose (Sigma) with either 1 µl of IVA12 mAb, 1 µl of VIC-Y1 mAb, or 25 µl of E1 antiserum. The immunoadsorbants were washed 5 times with buffer (50 mM Tris-HCl, pH 7.4, 150 mM NaCl, 5 mM EDTA, 0.05% Triton-X100, and 0.02% of $NAN_3$) and eluted with SDS sample buffer. The samples were analyzed by SDS-PAGE and autoradiography (Reyes et al., 1991).

Forty-five h after transfections with genes for mutant and wild type $I_i$ chains without HLA-DR $\alpha,\beta$ genes, the COS1 cells were labeled 3 h with [$^{35}$S]methionine, immunoprecipitates by E1 anti-$I_i$(183–193) serum were formed and digested with endoglycosidase H. The samples were examined by SDS-PAGE and autoradiography. The five $I_i$ mutant proteins were expressed as strongly as was wild type $I_i$. Because the $I_i$ chains were sensitive to endoglycosidase H treatment, they contained high mannose polysaccharide chains. They were presumably sequestered in the rough endoplasmic reticulum, without further processing of carbohydrate side chains, since Marks et al. (1990, *J. Cell Biol.*, 111:839–855) showed that $I_i$ can be sequestered in the rough endoplasmic reticulum without sialylation and with endoglycosidase H sensitivity when the $I_i$ is not bound to class II $\alpha,\beta$ chains. Since VIC-Y1 mAb did not recognize mutant [$R^{19}R^{20}$] while it did the other mutant and wild type $I_i$ chains (data not shown), that mutation presumably altered the VIC-Y1 determinant, thus further defining the apparent recognition site of VIC-Y1 at the N-terminus of $I_i$ (Quaranta, V. et al., 1984, *J. Immunol.*, 132:1900–1905).

Example 8

Cathepsin B Digestions of Mutant and Wild Type $I_i$

Cathepsin B digestions were carried out according to Reyes et al. (1991, *J. Immunol.*, 146:3877–3880). The cell lysate from about $5 \times 10^5$ cells in 150 µl was brought to pH 5.0 with 0.1 M sodium citrate (pH 2.5). The lysates were treated with cathepsin B in the presence of 1 mM DTT and 1 mM EDTA at room temperature for 1 h, or for other times as indicated. After enzymatic or control digestions, the samples were brought to pH 7.4 with 10 mM Tris (pH 9.5) containing 2 mM PMSF, 10 mM NEM, and 1 mM iodoacetamide and immunoprecipitates with IVA12 anti-MHC class II $\alpha,\beta$ chains were prepared in order to analyze $I_i$ fragments still bound to MHC class II $\alpha,\beta$ chains. In order to analyze $I_i$ fragments both bound to and released from MHC class II $\alpha,\beta$ chains, immunoprecipitates were digested under the same conditions as above in 30 µl volumes and the reactions were terminated with 3X SDS sample buffer (1X SDS sample buffer contained: 62.5 mM Tris-HCl, pH 6.8, 10% (w/v) glycerol, 5% 2-mercaptoethanol, and 2.3% SDS) and heating at 100° C. The samples were applied directly to the electrophoretic gels.

Immunoprecipitations with anti-MHC class II mAb IVA-12 of MHC class II $\alpha,\beta$ and $I_i$ triple transfectants demonstrated that wild type and all mutant $I_i$ chains associated with the class II $\alpha,\beta$ chains and formed approximately equal quantities of trimeric complexes. Digestions of these complexes with cathepsin B, however, revealed different patterns of $I_i$ cleavage (Table III). All of the mutants except [$R^{151}K^{154}$] had reduced levels or the absence of certain of the fragments occurring with cathepsin B digestion of wild type $I_i$. The principal wild type forms of $I_i$ seen with digestion of wild type $I_i$ were p21, p14, p10, and p6. In contrast to the wild type $I_i$ digestion pattern, mutant [$L^{174}F^{175}$] had a trace amount of p21 and mutant [$R^{78}K^{80}K^{83}K^{86}$] did not produce p14, p10, and p6. Also, mutants [$R^{19}R^{20}$] and [$K^{137}K^{143}$] had weak p21 bands which were about one tenth as strong as the wild type p21 band (comparing the patterns with 5 units cathepsin B with mutant [$R^{19}R^{20}$] and [$K^{137}K^{143}$] versus 0.5 unit cathepsin B with wild type $I_i$).

TABLE III

Appearance of fragments of wild type and mutant $I_i$ chains after digestion with cathepsin B.

| Wild Types or Mutant $I_i$ | CB FRAGMENTS | | | | CD FRAGMENTS | | | |
|---|---|---|---|---|---|---|---|---|
| | p21 | p14 | p10 | p6 | p21 | p14 | p10 | p6 |
| WT | + | + | + | + | + | + | + | + |
| M[$R^{19}$→A; $R^{20}$→A] | +/− | +/− | p12 | + | + | +/− | − | + |
| M[$R^{78}$→A; $K^{80}$→A; $K^{83}$→A; $K^{86}$→T] | + | − | − | − | + | − | − | − |
| M[$K^{137}$→A; $K^{143}$→A] | +/− | + | + | + | + | +/− | + | +/− |
| M[$R^{151}$→A; $K^{154}$→A] | + | +/− | + | + | + | + | + | + |
| M[$L^{174}$→V; $F^{175}$→A] | − | + | + | + | − | + | + | + |

The letters in parenthesis indicate where the mutations were made. For example, in M[$R^{19}$→A;$R^{20}$→A] the arginines in positions 19 and 20 were replaced by alanines. For simplicity throughout this disclosure, the replacing residue is omitted, e.g., [$R^{19}$→A;$R^{20}$→A] is abbreviated to [$R^{19}R^{20}$]. +/− indicates the band from the mutant $I_i$ is weaker than the corresponding one from WT $I_i$. Fragments of comparable size from digestions with CB or CD are not implied to be cleaved at identical sites.

The digestion patterns of wild type $I_i$ and mutant [$R^{78}K^{80}K^{83}K^{86}$] indicated that p14, p10, and p6 were degradation products of p21. In order to clarify the relationship among these smaller $I_i$ fragments one to another, the class II MHC $\alpha,\beta$ chain complexes with wild type or mutants $I_i$ chains were digested with a series of cathepsin B concentrations including the relatively high dose of 30 U/ml. At that cathepsin B dose, $I_i$ and all intermediate $I_i$ fragments were cleaved except for resistant p6 which was still associated with MHC class II $\alpha,\beta$ chains in immunoprecipitates with IVA-12 mAb to the $\alpha,\beta$ chains. This result and the finding that the integrated density of the high dose cathepsin B-generated p6 band was about the sum of the p14, p10 and p6 bands seen at lower dose cathepsin B digestions indicates that p6 is a degradation product of p14 and p10.

Previously it was reported that cathepsin B and cathepsin D cleaved and released $I_i$ from MHC class II molecules without apparent damage to the $\alpha,\beta$ chains (Reyes, V. E. et al., 1991, *J. Immunol.*, 146:3877–3880). However, in light of the finding that some $I_i$ mutants protect the class II $\beta$ chain from loss of 1–2 kilodaltons, it is clear that removal of wild type $I_i$ is associated with a cleavage of the $\beta$-chain presumably at $K^{12}$.

Example 9

Cathepsin D Digestion Patterns of Wild Type and Mutant $I_i$

CD digestions were carried out according to Reyes et al. (1991). The cell lysate from about $5\times10^5$ cells in 150 μl was brought to pH 5.0 with 0.1 M sodium citrate (pH 2.5). The lysates were treated with cathepsin D (Sigma) in the presence of 1 mM EDTA, at room temperature for 1 h, or for other times as indicated. After enzymatic or control digestions, the samples were brought to pH 7.4 with 10 mM Tris (pH 9.5) containing 2 mM PMSF, 10 mM NEM, and 1 mM iodoacetamide and immunoprecipitates were prepared to analyze $I_i$ fragments still bound to MHC class II α,β chains. In order to analyze $I_i$ fragments both bound to and released from MHC class II α,β chains immunoprecipitates were digested under the same conditions as above in 30 μl volumes and the reactions were terminated with 3X SDS sample buffer (1X SDS sample buffer contained: 62.5 mM Tris-HCl, pH 6.8, 10% (w/v) glycerol, 5% 2-mercaptoethanol, and 2.3% SDS) and heating at 100° C. The samples were applied directly to the electrophoretic gels.

Upon cathepsin D digestion of transfected trimers, p21 was produced from all of the mutant and wild type $I_i$, except for mutant $[L^{174}F^{175}[$ (Table III). $L^{173}L^{174}F^{175}$ thus appears to be a cathepsin D cleavage site. In mutant $[L^{174}F^{175}]$ actually more p14, p10, and p6 were produced, indicating that once the $L^{173}L^{174}F^{175}$ site was altered, other cathepsin D cleavage sites predominated and that these smaller fragments might be derived from p21. The $I_i$ fragmentation pattern of cathepsin D digestion generally paralleled that of cathepsin B digestion, probably because the cathepsin D sites were in the vicinity of cathepsin B sites. However, some differences were found. (1) Cathepsin D digestion did not lead to premature release of $I_i$ fragments. Mutants $[R^{78}K^{80}K^{83}K^{86}]$ and $[K^{137}K^{143}]$ were somewhat resistant to cathepsin D digestion and had reduced levels of p21 and increased intact $I_i$ relative to the observations with cathepsin B. (2) With these latter two mutants, the p21 band formed clearly upon cathepsin D digestion; but in the case of cathepsin B digestion, the p21 band was more of a smear.

Example 10

Increased Release of the Cathepsin B-Generated p21 $I_i$ Fragment from Some $I_i$ Mutants In order to examine whether the cathepsin B-derived p21 from mutants $[R_{19}R^{20}]$, $[K^{137}K^{143}]$, and $[L^{174}F^{175}]$ was produced, or degraded, or dissociated from HLA-DR1 α,β chains, class II α,β trimers were isolated by immunoprecipitation with IVA-12 mAb and then digested them with cathepsin B and analyzed all products by SDS-PAGE. Immunoprecipitates were digested under the same conditions as in Example 8 in 30 μl volumes and the reactions were terminated with 3X SDS sample buffer (1X SDS sample buffer contained: 62.5 mM Tris-HCl, pH 6.8, 10% (w/v) glycerol, 5% 2-mercaptoethanol, and 2.3% SDS) and heating at 100° C. The samples were applied directly to the electrophoretic gels.

Cathepsin B generated p21 from mutants $[R^{19}R^{20}]$ and $[K^{137}K^{143}]$ as strongly as it did with wild type $I_i$, indicating that p21 was produced from these two mutants but that it was promptly dissociated from DR1 α,β chains. In mutant $[K^{137}K^{143}]$, cathepsin B cleavage might occur at $R^{151}$ or $K^{154}$, or still at $K^{137}$ or $K^{143}$, to produce p21. However, the native conformation at or near $K^{137}K^{143}$ is the most preferred site for cathepsin B cleavage to produce p21 which is retained on the α,β chains. If cathepsin B does not cleave at $K^{137}K^{143}$ first, then $I_i$ dissociates from the MHC class II α,β chains. Mutation at $R^{19}R^{20}$ also led to premature release of p21 after cathepsin B digestion. In the case of mutant $[L^{174}F^{175}]$, p18 and p16 are produced instead of p21, suggesting that mutation at the $L^{174}F^{175}$ site prevents not only cathepsin D cleavage there but also the cathepsin B cleavage at $K^{137}K^{143}$. p18 and p16 were released from MHC class II α,β chains after they were produced. The patterns of low molecular weight bands in this experiment were similar to those after high dose cathepsin B digestions showing only p6, with little or no p14 and p10. Probably in these immunoprecipitations, there was less competitive inhibition by other lysate proteins, leading to patterns comparable to the high dose cathepsin B digestions.

Example 11

Inhibition of Antigen Presentation by PH-1.0 Peptide (SEQ. ID. NO: 16) and Enhancement of Antigen Presentation by $I_i$(148–164) (SEQ. ID. NO:2) and $I_i$ (78–92) (SEQ. ID. NO:1) Peptides Since the demonstration by DeLisi and Berzofsky that T cell-presented epitopes can be coiled as amphipathic helices (DeLisi, C. et al., 1985, *Proc. Natl. Acad. Sci. USA*, 82:7048–7052), theories for the selection of such epitopes based on mechanisms of such motifs have been tested (Margalit, H., et al., 1987, *J. Immunol.*, 138:2213–2229; Rothbard, J. B. et al., 1988, *EMBO J.*, 7:93–100; Stille, C. J. et al., 1987, *Mol. Immunol.*, 24:1021–1027; Reyes, V. E. et al., 1988, *Mol. Immunol.*, 25:867–871). Finding such a "perfect" amphipathic helix in $I_i$(146–164) led to the hypothesis that this helix was a surrogate antigen and was capable of blocking the peptide binding site of MHC class II molecules (Elliott, W. L. et al., 1987, *J. Immunol.*, 138:2949–2952; Stille, C. J. et al., 1987, *Mol. Immunol.*, 24:1021–1027). The synthetic peptide PH-1.0 (SEQ ID NO 17) was designed to mimic $I_i$(146–164) structurally in terms of having a narrow, longitudinal hydrophobic strip-of-helix. A series of analogs of PH-1.0 SEQ ID NO 16 have also been designed to test the effects of systematic substitutions of threonine for leucine within the longitudinal strip-of-helix on helical coiling of peptides against lipid micelles (Lu, S. et al., 1991, *J. Biol. Chem.*, 266:10054–10057).

The effect of PH-1.0 SEQ. ID. NO:16 on antigen presentation was tested in a functional assay. PH-1.0 SEQ ID NO:16 blocked the presentation of pigeon cytochrome C(81–104) peptide to specific, $E^k$-restricted TPc9.1 murine T cell hybridoma cells (Table IV). The competitive inhibition assay was carried out as follows. $5\times10^4$ paraformaldehyde-fixed CH27 B lymphoma cells (antigen presenting cells) were incubated in 96-well plates with $5\times10^4$ TPc9.1 T hybridoma cells (irradiated 2200 rads) for 24 hrs in the presence of 6 μM (81–104) antigenic peptide and different concentrations of the PH-1.0 peptide. Each condition was assayed in triplicate. After incubation, the response of the T cell hybridoma was determined by measuring the IL-2/IL-4 secreted during the 24 hr culture. Culture supernatants were collected and were tested for IL-2/IL-4 content by the ability to support the growth of the IL-2/IL-4-dependent cell line HT-2 as measured by the incorporation of [$^3$H]thymidine. The % inhibition was calculated as: 100 - [(CPM of T+APC+peptide+PH–1.0 / CPM of T+APC+peptide)×100].

TABLE IV

PH-1.0 (SEQ ID NO. 17) Inhibits the MHC Class II-Restricted Presentation of Antigenic Peptide to T cells

| PH-1.0 Concentration | 100 μM | 50 μM | 10 μM | 1 μM | 0 μM |
|---|---|---|---|---|---|
| % Inhibition | 100 | 98 | 61 | 10 | 0 |

$I_i$(148–163) (SEQ. ID. NO:2) and $I_i$(78–92) (SEQ. ID. NO:1) peptides enhanced responses to pigeon cytochrome C(81–104) peptide by the specific, $E^k$-restricted murine T cell hybridoma, TPc9.1 (Table V). The assay was carried out as follows. $5 \times 10^4$ paraformaldehyde-fixed CH27 B lymphoma cells (antigen presenting cells) were incubated in 96-well plates with $5 \times 10^4$ TPc9.1 T hybridoma cells (irradiated 2200 rads) for 24 hrs in the presence of: no peptides, 50 μM $I_i$ peptide only, 6 μM pigeon cytochrome C(81–104) peptide only, and 50 μM $I_i$ peptide plus 6 μM pigeon cytochrome C(81–104) peptide. Each condition was assayed in sextuplet. After incubation, the response of the T cell hybridoma was determined by measuring the IL-2/IL-4 secreted during the 24 hr culture. The supernatants were collected and were tested for IL-2/IL-4 content by the ability to support the growth of the IL-2/ IL-4-dependent cell line HT-2 as measured by [$^3$H]thymidine incorporation. The values presented in Table V are the CPM$\times 10^{-3}$ incorporated in the HT-2 indicator assay.

TABLE V $I_i$ Peptides Enhance the MHC Class II-Restricted Presentation of Pigeon Cytochrome C Peptide (81–104) to T cells

|  | $I_i$ (148–164) (SEQ ID NO. 2) | $I_i$ (78–92) (SEQ ID NO. 1) |
|---|---|---|
| (T+APC) | 5.4 | 5.4 |
| (T+APC) +$I_i$ peptide | 6.9 | 5.9 |
| (T+APC) +PGCC (81–104) | 50.8 | 50.8 |
| (T+APC) +$I_i$ peptide +PGCC (81–104) | 110.2 | 121.7 |

The enhancement of responses to pigeon cytochrome C peptide (81–104) by $I_i$(148–164) and $I_i$(78–92) was assayed as a function of concentration of the added $I_i$ peptide (Table VI). The values in the Table represent the % enhancement of the pigeon cytochrome C(81–104) peptide-specific, $E^k$-restricted response by the TPc9.1 murine T cell hybridoma (T) to the peptide presented by paraformaldehyde-fixed CH27 B lymphoma cells (APC). Culture supernatants were collected and were tested for IL-2/IL-4 content by the ability to support the growth of the Il-2/IL-4-dependent cell Line HT-2 as measured by the incorporation of [$^3$H]thymidine. The % enhancement was calculated as: [(CPM of T+APC+peptide+ $I_i$ peptide / CPM of T+APC+peptide)×100]−100.

TABLE VI $I_i$ Peptides Enhance the MHC Class II-Restricted Presentation of Antigenic Peptide to T cells

| Peptide Concentration | 100 μM | 50 μM | 10 μM | 1 μM | 0 μM |
|---|---|---|---|---|---|
| $I_i$ (148–164) (SEQ ID NO. 2) | 140 | 91 | 19 | 0 | 0 |
| $I_i$ (78–92) (SEQ ID NO. 1) | 170 | 187 | 101 | 40 | 0 |

EQUIVALENTS

Those skilled in the art will recognize, or be able to ascertain using no more than routine experimentation, many equivalents to the embodiments of the invention described specifically herein. Such equivalents are intended to be encompassed in the scope of the following claims.

REFERENCES

A. Original Papers Authored by Inventor

Elliott, W. L., Stille, C. J., Thomas, L. J. and Humphreys, R. E. An hypothesis on the binding of an amphipathic, α helical sequence in $I_i$ to the desetope of class II antigens. J. Immunol. 138:2949–2952, 1987.

Goldschmidt, T. G., Reyes, V. E., You, G., Nelson, D. J., Reisert, P. S., Anderson, J., Mole, J. and Humphreys, R. E. Adsorption and helical coiling of amphipathic peptides on lipid vesicles leads to negligible protection from cathepsin B or cathepsin D. Immunol. Invest. 22:25–40, 1993.

Lam, V., Thomas, L. J., Kostyal, D. A. and Humphreys, R. E. Highly conserved, potential cleavage sites about the desetopes of MHC class I and II molecules. Tissue Antigens 39:26–31, 1992.

Lu, S., Ciardelli, T., Reyes, V. E. and Humphreys, R. E. Number and placement ofhydrophobic residues in a longitudinal strip governs helix formation of peptides in the presence of lipid vesicles. J. Biol. Chem. 266:10054–10057, 1991.

Lu, S., Reyes, V. E., Lew, R. A., Anderson, J., Mole, J., Humphreys, R. E. and Ciardelli, T. Role of recurrent hydrophobic residues in catalysis of helix formation by T cell-presented peptides in the presence of lipid vesicles. J. Immunol. 145:899–904, 1990.

Nguyen, Q. V. and Humphreys, R. E. Time course of intracellular associations, processing, and cleavage of $I_i$ forms and class II MHC molecules. J. Biol. Chem. 264:1631–1637, 1989.

Nguyen, Q. V., Knapp, W. and Humphreys, R. E. Inhibition by leupeptin and antipain of the intracellular proteolysis of $I_i$. Human Immunol. 24:153–163, 1989.

Nguyen, Q.V., Roskey, A. M. and Humphreys, R. E. Effects of brefeldin A in cleavage of invariant chain to p21 and p10 and the appearance of $I_i$-freed class II MHC dimers. Mol. Immunol. 30:137–144, 1993.

Rennell, D., Poteete, A. R., Beaulieu, M., Kuo, D. Z., Lew, R. A. and Humphreys, R. E. Critical functional role of the COOH-terminal ends of longitudinal hydrophobic strips in α-helices of T4 lysozyme. J. Biol. Chem. 267:17748–17752, 1992.

Reyes, V. E., Chin, L. T. and Humphreys, R. E. Selection of class I MHC-restricted peptides with the strip-of-helix hydrophobicity algorithm. Mol. Immunol. 25:867–871, 1988.

Reyes, V. E., Fowlie, E. J., Lu, S., Phillips, L., Chin, L. T., Humphreys, R. E. and Lew, R. A. Comparison of three related methods to select T cell-presented sequences of protein antigens. Mol. Immunol. 27:1021–1027, 1990.

Reyes, V. E., Lu, S. and Humphreys, R. E. Binding of radioiodinated influenza virus peptides to class I MHC molecules and to other cellular proteins as analyzed by gel filtration and photoaffinity labeling. Mol. Immunol. 28:341–348, 1991.

Reyes, V. E., Lu, S. and Humphreys, R. E. Cathepsin B cleavage of $I_i$ from class II MHC α- and β-chains. J. Immunol. 146:3877–3880, 1991.

Reyes, V. E., Phillips, L., Humphreys, R. E. and Lew, R. A. Prediction of protein helices with a derivative of the stripof-helix hydrophobicity algorithm. J. Biol. Chem. 264:12854–12858, 1989.

Salomon, M., Adams, S., Pardanani, A., Vazquez, S., Humphreys, R. E. and Lew, R. A. Comparison of actual and random-frequency-model distributions of peptide scavenging and T cell-presented sites in antigenic proteins. Vaccine (in press).

Stille, C. J., Thomas, L. J., Reyes, V. E. and Humphreys, R. E. Hydrophobic strip-of-helix algorithm for selection of T cell-presented peptides. Mol. Immunol. 24:1021–1027, 1987.

Thomas, L. J., Humphreys, R. E., Knapp, W. and Nguyen, Q. V. Time-dependent cleavage of a high mannose form of $I_i$ to p25 in an intracellular compartment. Am. J. Hematol. 32:167–177, 1989.

Thomas, L. J., Nguyen, Q. V., Elliott, W. L. and Humphreys, R. E. Proteolytic cleavage of $I_i$ to p25. J. Immunol. 140:2670–2674, 1988.

Tiarks, C., Humphreys, R. E., Anderson, J., Mole, J. and Pechet, L. Hypothesis for the control of clotting factor VIII inhibitory antibodies by decreasing potency of helper T cell-recognized epitopes in Factor VIII. Scand. J. Immunol. 36:653–660, 1992.

Torgerson, R. R., Lew, R. A., Reyes, V. E., Hardy, L. and Humphreys, R. E. Highly restricted distributions of hydrophobic and charged amino acids in longitudinal quadrants of $\alpha$ helices. J. Biol. Chem. 266:5521–5524, 1991.

Vazquez, S. R., Kuo, D. Z., Bositis, C. M., Hardy, L. W., Lew, R. A. and Humphreys, R. E. Residues in the longitudinal, hydrophobic strip-of-helix relate to terminations and crossings of $\alpha$ helices. J. Biol. Chem. 267:7406–7410, 1992.

B. Review Articles by Inventor

Goldschmidt, T. G., Lu, S., Reyes, V. E., Lam, V., Torgerson, R. R., Nguyen, Q. V., Lew, R. A. and Humphreys, R. E. Toward engineering of T-cell-presented epitopes. In: *Vaccines 91, Modern Approaches to New Vaccines Including Prevention of AIDS* (R. M. Chanock, H. S. Ginsburg, F. Brown and R. A. Lerner, eds.), Cold Spring Harbor Laboratory press, Cold Spring Harbor, (N.Y.), pp. 339–343, 1991.

Lu, S., Reyes, V. E., Bositis, C. M., Goldschmidt, T. G., Lam, V., Sorli, C. H., Torgerson, R. R., Lew, R. A. and Humphreys, R. E. prediction of T cell-recognized epitopes in proteins. In: *Structure of Antigens* (M.H.V. Van Regenmortel, ed.), Telford press (NJ), pp. 81–98, 1992.

Lu, S., Reyes, V. E., Bositis, C. M., Goldschmidt, T. G., Lam, V., Torgerson, R. R., Ciardelli, T., Hardy, L., Lew, R. A. and Humphreys, R. E. Biophysical mechanisms of the scavenger site near T-cell presented epitopes. Vaccine 10:3–7, 1992.

Lu, S., Reyes, V. E., Torgerson, R. R., Lew, R. A. and Humphreys, R. E. Common principles in protein folding and antigen presentation. Trends in Biotechnology 9:238–242, 1991.

Reyes, V. E., Lew, R. A., Lu, S. and Humphreys, R. E. Prediction of $\alpha$ helices and T cell-presented sequences in proteins with algorithms based on the strip-of-helix hydrophobicity index. In: *Methods in Enzymology. Molecular Design and Modeling: Concepts and Applications* (J. L. Langone, ed.), Academic Press (NY), pp. 225–238, 1991.

PAPERS OF OTHER INVESTIGATORS

Bakke, O. and Dobberstein, B. MHC class II-associated invariant chain contains a sorting signal for endosomal compartment. Cell 63:707–716, 1990.

Blum, J. S. and Cresswell, P. Role for intracellular proteases in the processing and transport of class II antigens. Proc. Natl. Acad. Sci. USA 85:3975–3979, 1988.

Bond, J. S. Commercial available proteases. In *Proteolytic Enzymes: A Practical Approach*. Beynon, R. J. and Bond, J. S. eds., IRL Press, 1989, New York, p. 232.

Brown, J. H., Jardetzky, T., Saper, M. A., Samraoui, B., Bjorkman, P. J. and Wiley, D. C. A hypothetical model of the foreign antigen binding site of class II histocompatibility molecules. Nature 332:845–850, 1988.

Buus, S., Sette, A., Colon, S. M., Jenis, D. M. and Grey, H. M. Isolation and characterization of antigen-Ia complexes involved in T cell recognition. Cell 47:1071–1077, 1986.

Chicz, R. M., Urban, R. G., Lane, W. S., Gorga, J. C., Stern, L. J., Vignali, D. A. A. and Strominger, J. L. Predominant naturally processed peptides bound to HLA-DR1 are derived from MHC-related molecules and are heterogeneous in size. Nature 358:764–768, 1992.

Clements, V. K., Baskar, S., Armstrong, T. D. and Ostrand-Rosenberg, S. Invariant chain alters the malignant phenotype of MHC class $II^+$ tumor cells. J. Immunol. 149:2391–2396, 1992.

DeLisi, C. and Berzofsky, J. A. T-cell antigenic sites tend to be amphipathic structures. Proc. Natl. Acad. Sci. USA 82:7048–7052, 1985.

Diment, S. Different roles for thiol and aspartyl proteases in antigen presentation of ovalbumin. J. Immunol. 145:417–422, 1990.

Guagliardi, L. E., Koppelman, B., Blum, J. S., Marks, M. S., Cresswell, P. and Brodsky, F. M. Co-localization of molecules involved in antigen processing and presentation in an early endocytic compartment. Nature 343:133–139, 1990.

Ho, S. N., Hunt, H. D., Horton, R. M., Pullen, J. K. and Pease, L. Site-directed mutagenesis by overlap extension using the polymerase chain reaction. Gene 77:51–59, 1989.

Lanzavecchia, A., Reid, P. A. and Watts, C. Irreversible association of peptides with class II MHC molecules in living cells. Nature 357:249–252, 1992.

Lehmann, P. V., Forsthuber, T., Miller, A. and Sercarz, E. E. Spreading of T-cell autoimmunity to cryptic determinants of an autoantigen. Nature 358:155–157, 1992.

Long, E. O., Rosen-Bronson, S., Karp, D. R., Malnati, M., Sekaly, R. P. and Jaraquemada, D. Efficient cDNA expression vectors for stable and transient expression of HLA-DR in transfected fibroblast and lymphoid cells. Human Immunol. 31:229–235, 1991.

Lotteau, V., Teyton, L., Peleraux, A., Nilsson, T., Karlsson, L., Schmid, S. L., Quaranta, B. and Peterson, P. A. Intracellular transport of class II MHC molecules detected by invariant chain. Nature 348:600–605, 1990.

Machamer, C. E. and Cresswell, P. Biosynthesis and glycosylation of the invariant chain associated with HLA-DR antigens. J. Immunol. 29:2564–2569, 1982.

Margalit, H., Spouge, J. L., Cornette, J. L., Cease, K. B., DeLisi, C. and Berzofsky, J. A. Prediction of immunodominant helper T cell antigenic sites from the primary sequence. J. Immunol. 138:2213–2229, 1987.

Marks, M. S., Blum, J. S. and Cresswell, P. Invariant chain trimers are sequestered in the rough endoplasmic reticulum in the absence of association with HLA class II antigens. J. Cell Biol. 111:839–855, 1990.

Peterson, M. and Miller, J. Antigen presentation enhanced by the alternatively spliced invariant chain gene product p41. Nature 357:596–598, 1992.

Puri, J. and Factorovich, Y. Selective inhibition of antigen presentation to cloned T cells by protease inhibitors. J. Immunol. 141:3313–3319, 1988.

Quaranta, V., Majdic, O., Stingl, G., Liszka, K., Honigsmann, H. and Knapp, W. A human Ia cytoplasmic determinant located on multiple forms of invariant chain (gamma, gamma2, gamma3). J. Immunol. 132:1900–1905, 1984.

Roche, P. and Cresswell, P. High-affinity binding of an influenza hemagglutinin-derived peptide to purified HLA-DR. J. Immunol. 144:1849–1856, 1990.

Roche, P. and Cresswell, P. Invariant chain association with HLA-DR molecules inhibits immunogenic peptide binding. Nature 345:615–619, 1990.

Roche, P. and Cresswell, P. Proteolysis of the class II-associated invariant chain generates a peptide binding site in intracellular HLA-DR molecules. Proc. Natl. Acad. Sci. USA 88:3150–3154, 1991.

Rodriguez, G. M. and Diment, S. Role of cathepsin D in antigen presentation of ovalbumin. J. Immunol. 149:2894–2898, 1992.

Rothbard, J. B. and Taylor, W. R. A sequence pattern common to T cell epitopes. EMBO J. 7:93–100, 1988.

Rudensky, A. Y., Preston-Hurlburt, P., Hong, S-C., Barlow, A. and Janeway, Jr., C. A. Sequence analysis of peptides bound to MHC class II molecules. Nature 353:622–627, 1991.

Takahashi, H., Cease, K. B. and Berzofsky, J. A. Identification of proteases that process distinct epitopes on the same protein. J. Immunol. 142:2221–2226, 1989.

Teyton, L., O'Sullivan, D., Dickson, P. W., Lotteau, V., Sette, A., Fink, P. and Peterson, P. A. Invariant chain distinguishes between the exogenous and endogenous antigen presentation pathway. Nature 348:39–44, 1990.

Unanue, E. R. Antigen-presenting function of the macrophage. Ann. Rev. Immunol. 2:395–428, 1984.

Xu, M. and Stavnezer, J. EMBO J. 11:145–155, 1992.

---

I claim:
1. A method for enhancing presentation of an MHc class II restricted antigenic peptide to a T cell, comprising:
   a) forming a reaction mixture comprising:
      i) an MHC class II expressing antigen presenting cell;
      ii) the peptide YRMKLPKPPKPVSKMR (SEQ ID NO:1);

iii) the MHC class II restricted antigenic peptide which, when added to the incubation mixture, is not in association with an antigen presenting cell; and iv) a T cell which is responsive to the MHC class II restricted antigenic peptide of part iii); and b) incubating the reaction mixture of step a) under conditions appropriate for interaction between the antigen presenting cell and the T cell.

2. A method for enhancing presentation of an MHC class II restricted antigenic peptide to a T cell, comprising:

a) forming a reaction mixture comprising:
  i) an MHC class II expressing antigen presenting cell;
  ii) the peptide ENLRHLKNTMETLDWKV (SEQ ID NO:2);
  iii) the MHC Class II restricted antigenic peptide which, when added to the incubation mixture, is not in association with an antigenic presenting cell; and
  iv) a T cell which is responsive to the MHC Class II restricted antigenic peptide of part iii); and b) incubating the reaction mixture of step a) under conditions appropriate for interaction between the antigen presenting cell and the T cell.

3. A method for inhibiting presentation of an MHC class II restricted antigenic peptide to a T cell, comprising:

a) forming a reaction mixture comprising:
  i) an MHC class II expressing antigen presenting cell;
  ii) the peptide LYQELQKLTQTLK (SEQ ID NO:16);
  iii) the MHC Class II restricted antigenic peptide which, when added to the incubation mixture, is not in association with an antigen presenting cell; and
  iv) a T cell which is responsive to the MHC Class II restricted antigenic peptide of part iii); and b) incubating the reaction mixture of step a) under conditions appropriate for interaction between the antigen presenting cell and the T cell.

* * * * *

UNITED STATES PATENT AND TRADEMARK OFFICE
CERTIFICATE OF CORRECTION

PATENT NO.  : 5,559,028
DATED       : September 24, 1996
INVENTOR(S) : Robert E. Humphreys It is certified that error appears in the above-indentified patent and that said Letters Patent is hereby corrected as shown below:

On the title page, amend the title as shown below:

METHODS OF ENHANCING OR <u>INHIBITING</u> ANTIGEN PRESENTATION TO T CELLS [INHIBITING]

In the last sentence of the Abstract, delete "enchance" and substitute therefor ---enhance---.

In the Claims:

In Claim 3, amend step i) as shown below:

i)  an $\underline{E^k}$ MHC class II expressing antigen presenting cell

Signed and Sealed this

Sixteenth Day of September, 1997

Attest:

BRUCE LEHMAN

Attesting Officer        Commissioner of Patents and Trademarks

SEQUENCE LISTING ( 1 ) GENERAL INFORMATION:

( i i i ) NUMBER OF SEQUENCES: 16

( 2 ) INFORMATION FOR SEQ ID NO:1:

( i ) SEQUENCE CHARACTERISTICS:
( A ) LENGTH: 16 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:1:

Tyr Arg Met Lys Leu Pro Lys Pro Pro Lys Pro Val Ser Lys Met Arg
1               5                   10                  15

( 2 ) INFORMATION FOR SEQ ID NO:2:

( i ) SEQUENCE CHARACTERISTICS:
( A ) LENGTH: 17 amino acids
( B ) TYPE: amino acid
( C ) STRANDEDNESS: single
( D ) TOPOLOGY: linear ( i i ) MOLECULE TYPE: peptide ( x i ) SEQUENCE DESCRIPTION: SEQ ID NO:2:

Glu Asn Leu Arg His Leu Lys Asn Thr Met Glu Thr Leu Asp Trp Lys
1               5                   10                  15
Val ( 2 ) INFORMATION FOR SEQ ID NO:3:

( i ) SEQUENCE CHARACTERISTICS:
( A ) LENGTH: 216 amino acids
( B ) TYPE: amino acid
( C ) STRANDEDNESS: single
( D ) TOPOLOGY: linear ( i i ) MOLECULE TYPE: protein ( x i ) SEQUENCE DESCRIPTION: SEQ ID NO:3:

Met Asp Asp Gln Arg Asp Leu Ile Ser Asn Asn Glu Gln Leu Pro Met
1               5                   10                  15

Leu Gly Arg Arg Pro Gly Ala Pro Glu Ser Lys Cys Ser Arg Gly Ala

```
            20                          25                          30
Leu  Tyr  Thr  Gly  Phe  Ser  Ile  Leu  Val  Thr  Leu  Leu  Leu  Ala  Gly  Gln
          35                      40                 45
Ala  Thr  Thr  Ala  Tyr  Phe  Leu  Tyr  Gln  Gln  Gln  Gly  Arg  Leu  Asp  Lys
     50                      55                      60
Leu  Thr  Val  Thr  Ser  Gln  Asn  Leu  Gln  Leu  Glu  Asn  Leu  Arg  Met  Lys
65                           70                 75                           80
Leu  Pro  Lys  Pro  Pro  Lys  Pro  Val  Ser  Lys  Met  Arg  Met  Ala  Thr  Pro
                    85                      90                      95
Leu  Leu  Met  Gln  Ala  Leu  Pro  Met  Gly  Ala  Leu  Pro  Gln  Gly  Pro  Met
               100                      105                 110
Gln  Asn  Ala  Thr  Lys  Tyr  Gly  Asn  Met  Thr  Glu  Asp  His  Val  Met  His
               115                      120                 125
Leu  Leu  Gln  Asn  Ala  Asp  Pro  Leu  Lys  Val  Tyr  Pro  Pro  Leu  Lys  Gly
     130                      135                 140
Ser  Phe  Pro  Glu  Asn  Leu  Arg  His  Leu  Lys  Asn  Thr  Met  Glu  Thr  Leu
145                      150                      155                      160
Asp  Trp  Lys  Val  Phe  Glu  Ser  Trp  Met  His  His  Trp  Leu  Leu  Phe  Glu
                    165                      170                 175
Met  Ser  Arg  His  Ser  Leu  Glu  Gln  Lys  Pro  Thr  Asp  Ala  Pro  Pro  Lys
               180                      185                 190
Glu  Ser  Leu  Glu  Leu  Glu  Asp  Pro  Ser  Ser  Gly  Leu  Gly  Val  Thr  Lys
          195                      200                 205
Gln  Asp  Leu  Gly  Pro  Val  Pro  Met
     210                      215
```

( 2 ) INFORMATION FOR SEQ ID NO:4:

( i ) SEQUENCE CHARACTERISTICS:
        ( A ) LENGTH: 21 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:4:

CAGGTCGACT CTAGACGATC C                                          21

( 2 ) INFORMATION FOR SEQ ID NO:5:

( i ) SEQUENCE CHARACTERISTICS:
        ( A ) LENGTH: 25 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:5:

GTAGGATCCT GTGTGGGGCT GGCAG                                25

( 2 ) INFORMATION FOR SEQ ID NO:6:

( i ) SEQUENCE CHARACTERISTICS:
        ( A ) LENGTH: 17 base pairs
        ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:6:

CTGGGCGCGG CCCCTGG                                                                    17

(2) INFORMATION FOR SEQ ID NO:7:

(i) SEQUENCE CHARACTERISTICS:
        (A) LENGTH: 17 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:7:

CCAGGGGCCG CGCCCAG                                                                    17

(2) INFORMATION FOR SEQ ID NO:8:

(i) SEQUENCE CHARACTERISTICS:
        (A) LENGTH: 27 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:8:

CATGGCGCTT CCCGCGCCTC CCACGCC                                                         27

(2) INFORMATION FOR SEQ ID NO:9:

(i) SEQUENCE CHARACTERISTICS:
        (A) LENGTH: 22 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:9:

CGCGGGAAGC GCCATCGCCA GG                                                              22

(2) INFORMATION FOR SEQ ID NO:10:

(i) SEQUENCE CHARACTERISTICS:
        (A) LENGTH: 20 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:10:

GTGTACCCGC CACTGGCGGG                                                                 20

(2) INFORMATION FOR SEQ ID NO:11:

(i) SEQUENCE CHARACTERISTICS:
        (A) LENGTH: 19 base pairs
        (B) TYPE: nucleic acid
        (C) STRANDEDNESS: double
        (D) TOPOLOGY: linear (ii) MOLECULE TYPE: DNA (genomic)

(xi) SEQUENCE DESCRIPTION: SEQ ID NO:11:

TGGCGGGTAC ACCGCCAGG                                                                  19

(2) INFORMATION FOR SEQ ID NO:12:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:12:

CTGGCACACC TTGCGAAC                                     18

( 2 ) INFORMATION FOR SEQ ID NO:13:

( i ) SEQUENCE CHARACTERISTICS:
    ( A ) LENGTH: 18 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:13:

GTTCGCAAGG TGTGCCAG                                     18

( 2 ) INFORMATION FOR SEQ ID NO:14:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:14:

GGCTCCTGGC TGAAATG                                      17

( 2 ) INFORMATION FOR SEQ ID NO:15:

( i ) SEQUENCE CHARACTERISTICS:
    ( A ) LENGTH: 17 base pairs
    ( B ) TYPE: nucleic acid
    ( C ) STRANDEDNESS: double
    ( D ) TOPOLOGY: linear ( i i ) MOLECULE TYPE: DNA (genomic)

( x i ) SEQUENCE DESCRIPTION: SEQ ID NO:15:

CATTTCAGCC ACGAGCC                                      17

( 2 ) INFORMATION FOR SEQ ID NO:16:

( i ) SEQUENCE CHARACTERISTICS:
    ( A ) LENGTH: 13 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:16:

Leu Tyr Gln Glu Leu Gln Lys Leu Thr Gln Thr Leu Lys
1               5                   10